(12) United States Patent
Costa et al.

(10) Patent No.: US 8,335,590 B2
(45) Date of Patent: Dec. 18, 2012

(54) SYSTEM AND METHOD FOR ADJUSTING AN IMAGE CAPTURING DEVICE ATTRIBUTE USING AN UNUSED DEGREE-OF-FREEDOM OF A MASTER CONTROL DEVICE

(75) Inventors: Michael Costa, San Francisco, CA (US); David Robinson, Mountain View, CA (US); Michael L. Hanuschik, Mountain View, CA (US); Randal P. Goldberg, San Jose, CA (US); Paul Millman, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1026 days.

(21) Appl. No.: 12/342,230

(22) Filed: Dec. 23, 2008

(65) Prior Publication Data

US 2010/0161129 A1 Jun. 24, 2010

(51) Int. Cl.
*G05B 21/00* (2006.01)
(52) U.S. Cl. ........ 700/259; 700/245; 700/250; 700/251; 700/258; 700/263; 700/264; 901/47
(58) Field of Classification Search .................. 700/259, 700/263; 901/47
See application file for complete search history.

(56) References Cited

U.S. PATENT DOCUMENTS

| | | | |
|---|---|---|---|
| 6,424,885 B1 | 7/2002 | Niemeyer et al. | |
| 6,493,608 B1 | 12/2002 | Niemeyer | |
| 6,799,065 B1* | 9/2004 | Niemeyer | 600/407 |
| 2006/0241414 A1* | 10/2006 | Nowlin et al. | 600/431 |
| 2008/0094358 A1* | 4/2008 | Sullivan | 345/161 |
| 2008/0214306 A1* | 9/2008 | Ludden | 463/37 |

OTHER PUBLICATIONS

Vertut, Jean et al., Robot Technology: Teleoperation and Robotics Evolution and Development, 1986, vol. 3A, 332 pages, English translation Prentice-Hall, Inc., Inglewood Cliffs, NJ, USA.

* cited by examiner

*Primary Examiner* — Mary Cheung
*Assistant Examiner* — Jerrah Edwards

(57) ABSTRACT

An image capturing device is robotically positioned and oriented in response to operator manipulation of a master control device. An unused degree-of-freedom of the master control device is used to adjust an attribute such as focusing of the image capturing device relative to a continually updated setpoint. A deadband is provided to avoid inadvertent adjusting of the image capturing device attribute and haptic feedback is provided back to the master control device so that the operator is notified when adjusting of the attribute is initiated.

30 Claims, 9 Drawing Sheets

SYSTEM AND METHOD FOR ADJUSTING AN IMAGE CAPTURING DEVICE ATTRIBUTE USING AN UNUSED DEGREE-OF-FREEDOM OF A MASTER CONTROL DEVICE

FIELD OF THE INVENTION

The present invention generally relates to medical robotic systems and in particular, to a system and method for adjusting an image capturing device attribute using an unused degree-of-freedom of a master control device.

BACKGROUND OF THE INVENTION

Medical robotic systems such as those used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for minimally invasive surgery using such medical robotic systems is strong and growing.

Examples of medical robotic systems include the da Vinci® Surgical System and the da Vinci® S™ Surgical System from Intuitive Surgical, Inc., of Sunnyvale, Calif. Each of these systems includes a surgeon's console, a patient-side cart, a high performance three-dimensional ("3-D") vision system, and Intuitive Surgical's proprietary EndoWrist® articulating instruments, which are modeled after the human wrist so that when added to the motions of manipulators holding the surgical instruments, they allow at least six degrees of freedom of motion, which is comparable to or even greater than the natural motions of open surgery.

The da Vinci® surgeon's console has a high-resolution stereoscopic video display with two progressive scan cathode ray tubes ("CRTs"). The system offers higher fidelity than polarization, shutter eyeglass, or other techniques. Each eye views a separate CRT presenting the left or right eye perspective, through an objective lens and a series of mirrors. The surgeon sits comfortably and looks into this display throughout surgery, making it an ideal place for the surgeon to display and manipulate 3-D intraoperative imagery.

The patient-side cart typically includes three or more robotic arm assemblies with corresponding slave manipulators for holding and manipulating medical devices such as surgical instruments and image capturing devices for performing and/or viewing a medical procedure at a surgical site within a patient. To manipulate these medical devices, the surgeon's console also includes input devices which may be selectively associated with the medical devices and their respective slave manipulators. Since the movements of the input devices and their associated medical devices are scaled, this allows the surgeon to perform intricate medical procedures with greater ease than conventional open surgery. Further, it may even allow the surgeon to perform medical procedures that are not even feasible using conventional open surgery techniques.

During or before performing a medical procedure at a work site in a patient, it may be necessary or desirable to position and/or orient an image capturing device, such as a stereoscopic endoscope or ultrasound probe, so as to provide the surgeon a better view of the procedure on the display screen. Because the image capturing device generally has fewer degrees-of-freedom than a master control used for such positioning and orienting, unused degrees-of-freedom of the master control are available for control and other purposes. As an example, U.S. Pat. No. 6,799,065 entitled "Image Shifting Apparatus and Method for a Telerobotic System," which is incorporated herein by this reference, describes the possible use of an unused degree-of-freedom of a master control for focus or zoom control of a camera.

A number of practical problems may need to be overcome, however, in order to employ an unused degree-of-freedom of a master control for adjusting an attribute of an image capturing device where the master control is also associated at the time with the image capturing device for positioning and/or orienting the image capturing device. For example, one problem with such employment is that the controlling of the positioning and/or orienting of the image capturing device may result in a set-point of the unused degree-of-freedom changing. Another problem is possible inadvertent movement of the unused degree of freedom by the human operator using the master control.

OBJECTS AND SUMMARY OF THE INVENTION

Accordingly, one object of one or more aspects of the present invention is a system and method for adjusting an image capturing device attribute, such as focus, zoom, brightness, contrast, and the like, using an unused degree-of-freedom of a master control device.

Another object of one or more aspects of the present invention is a system and method for adjusting an image capturing device attribute using an unused degree-of-freedom of a master control device that automatically compensates for set-point changes of the unused degree-of-freedom.

Another object of one or more aspects of the present invention is a system and method for adjusting an image capturing device attribute using an unused degree-of-freedom of a master control device without inadvertent employment by an operator of the master control device.

These and additional objects are accomplished by the various aspects of the present invention, wherein briefly stated, one aspect is a medical robotic system comprising: an image capturing device manipulatable relative to a first reference frame in a first plurality of degrees-of-freedom; a first master control device manipulatable relative to a second reference frame in a second plurality of degrees-of-freedom; and a controller adapted to command manipulation of the image capturing device in each of the first plurality of degrees-of-freedom according to input received from the first master control device using less than all of the second plurality of degrees-of-freedom, determine a set-point for an unused one of the second plurality of degrees-of-freedom, and adjust an attribute of the image capturing device in response to manipulation of the first master control device in the unused one of the second plurality of degrees-of-freedom relative to the set-point.

Another aspect is a method for adjusting an attribute of an image capturing device that is robotically manipulatable relative to a first reference frame in a first plurality of degrees-of-freedom, comprising: controlling robotic manipulation of the image capturing device in each of the first plurality of degrees-of-freedom according to at least an input received from a first master control device manipulatable in a second reference frame in a second plurality of degrees-of-freedom, wherein the robotic manipulation of the image capturing device uses less than all of the second plurality of degrees-of-freedom; determining a set-point for an unused one of the second plurality of degrees-of-freedom; and adjusting the attribute of the image capturing device in response to manipulation of the first master control device in the unused one of the second plurality of degrees-of-freedom relative to the set-point.

Another aspect is a medical robotic system comprising: an image capturing device; a slave manipulator adapted to manipulate the image capturing device in four degrees-of-freedom; first and second master control devices each manipulatable in six degrees-of-freedom about its pivot point and cooperatively manipulatable in six degrees-of-freedom about a mid-point between the pivot points of the first and second master control devices; and a controller adapted to command manipulation of the image capturing device according to the cooperative manipulation of the first and second master control devices, determine a set-point of an unused one of the six degrees-of-freedom of the first master control device, and adjust an attribute of the image capturing device in response to manipulation of the first master control device in the unused one of the six degrees-of-freedom relative to the set-point.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
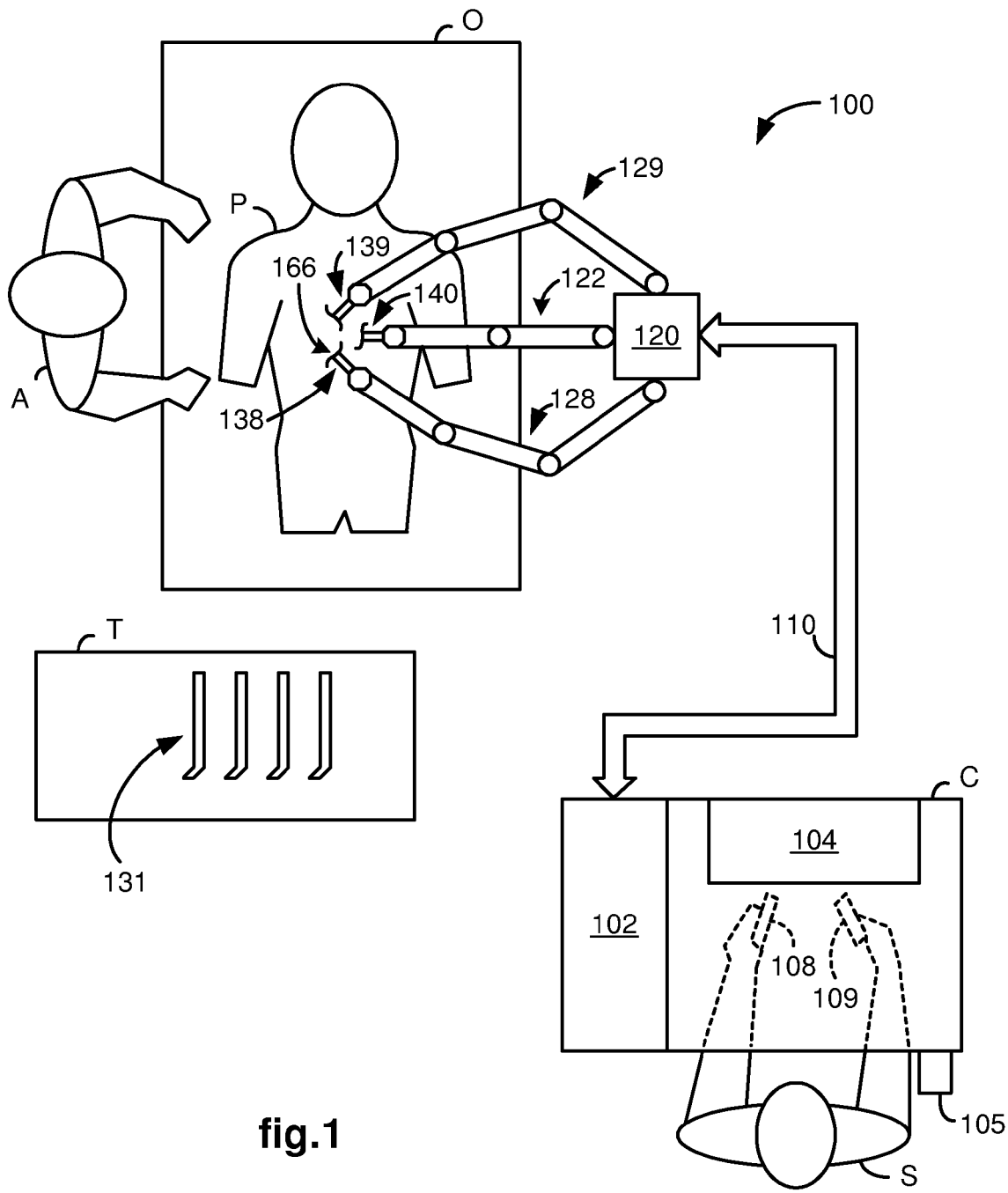
FIG. 1 illustrates a top view of an operating room employing a medical robotic system utilizing aspects of the present invention.

FIG. 1 illustrates, as an example, a top view of an operating room employing a medical robotic system. The medical robotic system in this case is a minimally invasive robotic surgical system 100 including a Console ("C") utilized by a Surgeon ("S") while performing a medical procedure, such as a diagnostic or surgical procedure, with assistance from one or more Assistants ("A"), on a Patient ("P") who is reclining on an Operating table ("O").

The Console includes a 3-D monitor 104 for displaying a 3-D image of a surgical site to the Surgeon, left and right manipulatable master controls 108, 109, a foot pedal 105, and a processor 102. The master controls 108, 109 may include any one or more of a variety of input devices such as joysticks, gloves, trigger-guns, hand-operated controllers, or the like. The processor 102 may be a dedicated computer integrated into the Console or positioned next or near to it, or it may be broken up into a number of processing or controller components that are distributed in a distributed processing fashion throughout the system 100.

The Surgeon performs a medical procedure by manipulating the master control devices 108, 109 (also referred to herein as "master manipulators" and "master controls") so that the processor 102 causes slave manipulators of their respectively associated robotic arm assemblies 128, 129 to manipulate their respective removably coupled surgical instruments 138, 139 (also referred to herein as "tools") accordingly, while the Surgeon views the surgical site in 3-D on the Console monitor 104 as it is captured by an image capturing device 140.

Each of the tools 138, 139, as well as the image capturing device 140 (also referred to herein simply as a "camera" for convenience, but understood to include all known image capturing devices such as a stereoscopic endoscope and ultrasound probe) is conventionally inserted through a tool guide (not shown) into the Patient so as to extend down to the surgical site through a corresponding minimally invasive incision such as Incision 166. The number of surgical tools used at one time and consequently, the number of robotic arms being used in the system 100 will generally depend on the medical procedure being performed and the space constraints within the operating room, among other factors. If it is necessary to change a tool being used during a procedure, the Assistant may remove the tool no longer being used from its robotic arm assembly, and replace it with another tool 131 from a Tray ("T") in the operating room.

Each of the robotic arm assemblies 122, 128, 129 is mounted on cart 120 and includes a slave manipulator and setup arms. The slave manipulators are robotically moved using motor controlled joints (also referred to herein as "active joints") in order to manipulate and/or move their respectively held medical devices. The setup arms may be manually manipulated by releasing normally braked joints (also referred to herein as "setup joints") to horizontally and vertically position the robotic arm assemblies 122, 128, 129 so that their respective medical devices may be inserted into their respective tool guides.

Preferably, the monitor 104 is positioned near the Surgeon's hands so that it will display a projected image that is oriented so that the Surgeon feels that he or she is actually looking directly down onto the operating site. To that end, images of the tools 138, 139 preferably appear to be located substantially where the Surgeon's hands are located.

The processor 102 performs various functions in the system 100. One important function that it performs is to translate and transfer the mechanical motion of master controls 108, 109 to their respective slave manipulators of robotic arm assemblies 128, 129 through control signals over bus 110 so that the Surgeon can effectively manipulate their respective tools 138, 139. Another important function is to implement various controllers, controls and methods described herein.

Although described as a processor, it is to be appreciated that the processor 102 may be implemented in practice by any combination of hardware, software and firmware. Also, its functions as described herein may be performed by one unit, or divided up among different components, each of which may be implemented in turn by any combination of hardware, software and firmware.

For additional details on the construction and operation of medical robotic systems such as described herein, see, e.g., U.S. Pat. No. 6,493,608 "Aspects of a Control System of a Minimally Invasive Surgical Apparatus," and U.S. Pat. No. 6,424,885 "Camera Referenced Control in a Minimally Invasive Surgical Apparatus," which are incorporated herein by reference.

Figure 2:
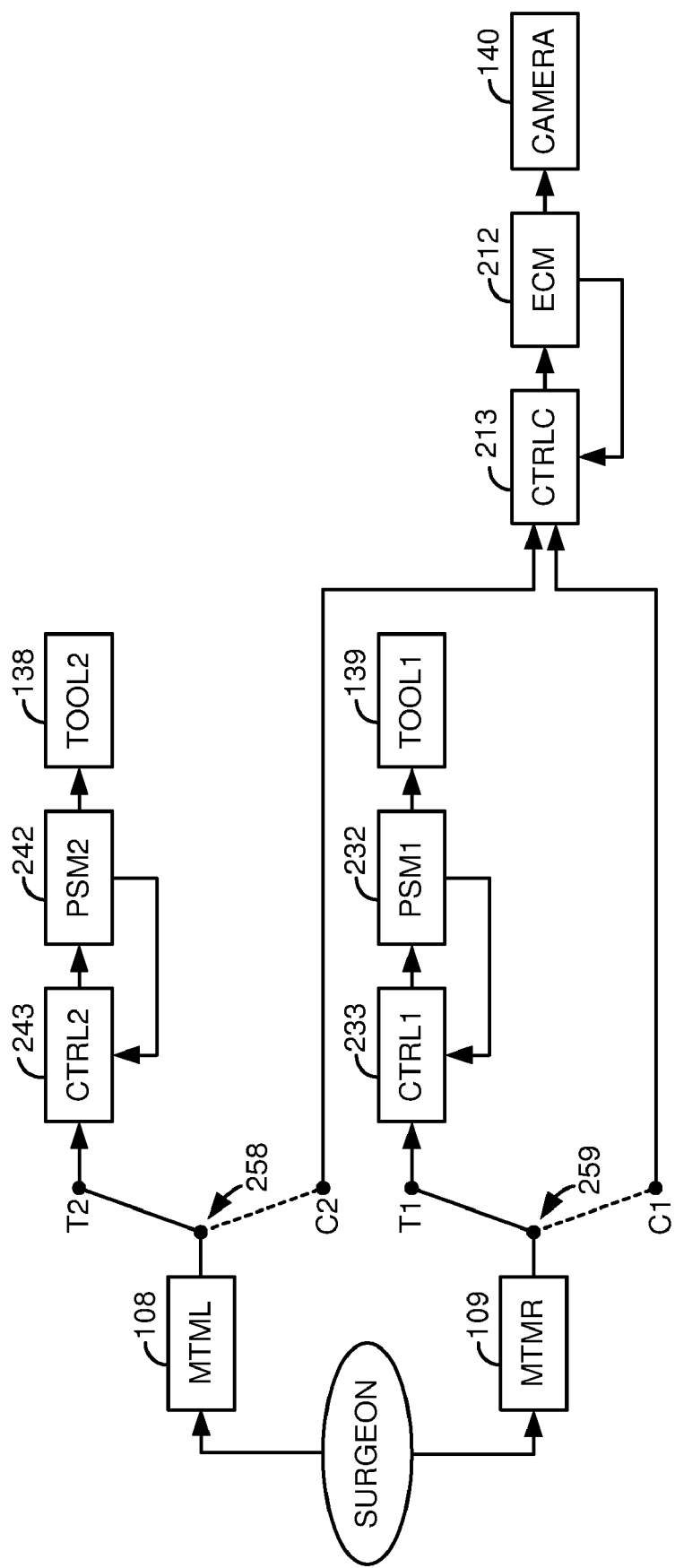
FIG. 2 illustrates a block diagram of a medical robotic system utilizing aspects of the present invention.

FIG. 2 illustrates, as an example, a block diagram of components for controlling and selectively associating device manipulators to the master controls 108, 109. Various surgical tools such as graspers, cutters, and needles may be used to perform a medical procedure at a work site within the Patient. In this example, two surgical tools 138, 139 are used to robotically perform the procedure and the camera 140 is used to view the procedure.

Each of the medical devices 138, 139, 140 is manipulated by its own manipulator. In particular, the camera 140 is manipulated by a camera manipulator (ECM) 212, the first surgical tool 139 is manipulated by a first tool manipulator (PSM1) 232, and the second surgical tool 138 is manipulated by a second tool manipulator (PSM2) 242.

In this example, each of the master controls 108, 109 may be selectively associated with either the camera 140 or one of the surgical tools 138, 139 so that the associated device may be controlled by the input device through its controller and manipulator. For example, by placing switches 258, 259 in their respective tool following modes "T2" and "T1", the left and right master controls 108, 109 may be respectively associated with the surgical tools 139, 138, which are telerobotically controlled through their respective controllers 233, 243 and manipulators 232, 242 so that the Surgeon may perform a medical procedure on the Patient while the camera 140 is soft-locked in place by its controller 213.

When the camera 140 is to be repositioned by the Surgeon, either one or both of the left and right master controls 108, 109 may be associated with the camera 140 so that the Surgeon may move the camera 140 through its controller 213 and manipulator 212. In this case, the disassociated one(s) of the surgical tools 138, 139 is/are soft-locked in place by its/their controller(s). For example, by placing switches 258, 259 respectively in camera positioning modes "C2" and "C1", the left and right master controls 108, 109 may be associated with the camera 140, which is telerobotically controlled through its controller 213 and manipulator 212 so that the Surgeon may position the camera 140 while the surgical tools 138, 139 are soft-locked in place by their respective controllers 233, 243. If only one input device is to be used for positioning the camera, then only one of the switches 258, 259 is placed in its camera positioning mode while the other one of the switches 258, 259 remains in its tool following mode so that its respective input device may continue to control its associated surgical tool.

The selective association of the master controls 108, 109 to other devices in this example may be performed by the Surgeon using a Graphical User Interface (GUI), a voice recognition system, or any other conventional manner operable through the Surgeon Console. Alternatively, the association of the master controls 108, 109 may be changed by the Surgeon depressing a button on one of the master controls 108, 109 or depressing the foot pedal 105, or using any other well known mode switching technique.

The present invention is particularly useful when the switches 258, 259 are both placed in their respective camera positioning modes "C2" and "C1" and an "image referenced control" scheme is employed to control Surgeon positioning and orienting of the camera's tip using the master controls 108, 109 in a "virtual handlebar" fashion.

Figure 3:
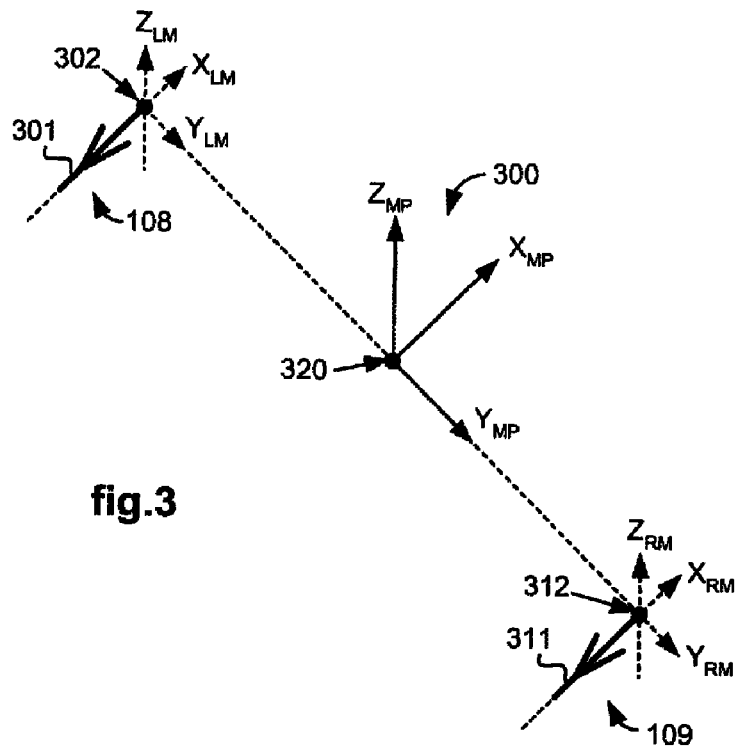
FIG. 3 illustrates master control device reference frames and corresponding degrees-of-freedom in a medical robotic system utilizing aspects of the present invention.

FIG. 3 illustrates, as an example, reference frames and corresponding degrees-of-freedom for the master controls 108, 109. Each of the master controls 108, 109 has a respective pivot point 302, 312 (also referred to as a "control point") and a reference frame centered at the pivot point. The master controls 108, 109 provide three translational degrees-of-freedom movement (e.g., forward/back along their respective longitudinal axes $X_{LM}$, $X_{RM}$ of their grippers 301, 311; side-to-side along first axes $Y_{LM}$, $Y_{RM}$ orthogonal to the longitudinal axes $X_{LM}$, $X_{RM}$; and up/down along second axes $Z_{LM}$, $Z_{RM}$ orthogonal to the first axes $Y_{LM}$, $Y_{RM}$ and longitudinal axes $X_{LM}$, $X_{RM}$) relative to their respective pivot points 302, 312 of their grippers 301, 311. The master controls 108, 109 also provide three orientational degrees-of-freedom movement (e.g., roll about their respective longitudinal axes $X_{LM}$, $X_{RM}$; pitch about their respective first axes $Y_{LM}$, $Y_{RM}$; and yaw about their respective second axes $Z_{LM}$, $Z_{RM}$) relative to their respective pivot points 302, 312 of their grippers 301, 311. In addition, squeezing their respective grippers 301, 311 may provide additional degrees-of-freedom for manipulating end effectors of surgical tools respectively associated with the master controls 108, 109 when in tool following mode.

In this example, both master controls 108, 109 are used to move the camera 140 as the Surgeon views images captured by the camera 140. Thus, an "image referenced control" is used in which the Surgeon is given the impression that he or she is moving the image captured by the camera 140. In particular, the Surgeon is provided with the sensation that he or she is grasping the image being displayed on the monitor 104 with his or her left and right hands and moving the image about the work site to a desired viewing point.

Figure 4:
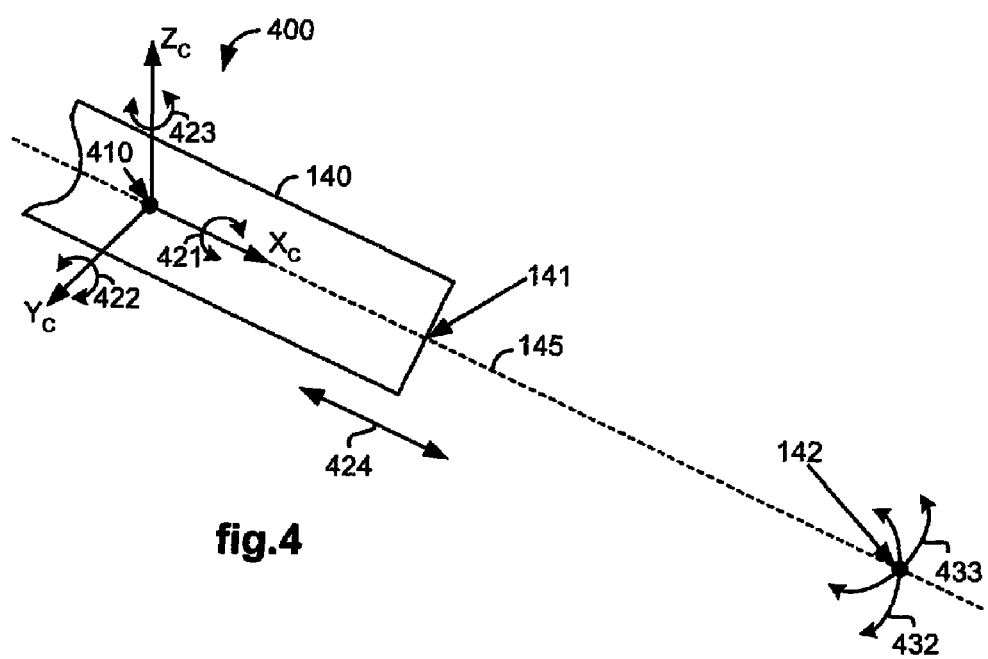
FIG. 4 illustrates a camera control reference frame and corresponding degrees-of-freedom in a medical robotic system utilizing aspects of the present invention.

FIG. 4 illustrates, as an example, a reference frame 400 and corresponding degrees-of-freedom for controlling movement of a tip of the camera 140. In this case, the camera tip 141 may be pivoted about a pivot point 410 (also referred to as a "fulcrum" and "remote center") in roll 421 about an axis $X_C$ extending along a longitudinal axis 145 of the camera 140 and/or its entry guide (not shown), in pitch 422 about an axis $Y_C$ (which is orthogonal to the $X_C$ axis), and in yaw 423 about an axis $Z_C$ (which is orthogonal to both the $X_C$ and $Y_C$ axes), as well as inserted/retracted 424 along the longitudinal axis 145 by operation of the camera manipulator 212 so as to provide four degrees-of-freedom movement. The longitudinal axis 145 centrally extends through the proximal and distal ends of the camera 140. A focal point 142 of the camera 140 moves along a surface of a sphere (having a radius defined by the insertion distance of the camera tip 141 from the remote center 410 and the focal length) as the camera tip 141 is moved in pitch and yaw (i.e., along arc 432 when the camera tip 141 is moved in pitch 422 and along arc 433 when the camera tip 141 is moved in yaw 423).

To control movement in the four degrees-of-freedom of the camera tip 141, a "virtual handlebar" scheme using the pair of master controls 108, 109 is used in which the two master controls are constrained to move together in a prescribed manner. Referring back to FIG. 3, the "virtual handlebar" employs a reference frame 300 having its origin at a midpoint 320 which is half-way between the pivot points 302, 312 of the master controls 108, 109. The Y-axis $Y_{MP}$ of the frame 300 is along a line intersecting the pivot points 302, 312, the Z-axis $Z_{MP}$ is in a vertical direction orthogonal to the Y-axis $Y_{MP}$, and the X-axis $X_{MP}$ is in a forward/back direction that is orthogonal to both the Y-axis $Y_{MP}$ and the Z-axis $Z_{MP}$.

The "virtual handlebar" reference frame 300 is related to the camera control reference frame 400 so that movement relative to the mid-point 320 by the master controls 108, 109 results in movement of the camera tip 141 relative to the remote center 410. In particular, as the mid-point 320 is moved forward/back in the $X_{MP}$ direction by moving both master controls 108, 109 forward/back, the camera controller 213 commands the camera manipulator 212 to move the camera 140 forward/back in the $X_C$ direction. Also, as the left master control 108 is moved up/down and the right master control 109 is moved in an opposite direction relative to the $Z_{MP}$ axis, the camera controller 213 commands the camera manipulator 212 to rotate the camera 140 in roll about the $X_C$ axis. Further, as the left master control 108 is moved forward/back and the right master control 109 is moved in an opposite direction relative to the $X_{MP}$ axis, the camera controller 213 commands the camera 140 to rotate in yaw about the $Z_C$ axis. Finally, as both the left and right master controls 108, 109 are pivoted together about their respective pivot points 302, 312 in the same direction, the camera controller 213 commands the camera manipulator 212 to rotate the camera 140 in pitch about the $Y_C$ axis.

Note that in using the "virtual handlebar" scheme as described above there are several unused degrees-of-freedom for each of the master controls 108, 109. For example, the master roll for each master control is unused (i.e., rotation of its gripper about its X-axis). Since the gripper's master roll resembles a dial to the Surgeon, it potentially can be used to turn on and adjust an attribute of an image capturing device such as a camera's focus, zoom, brightness, contrast, etc., in a similar manner as a radio's volume dial may turn on the radio and adjust its volume.

Figure 5:
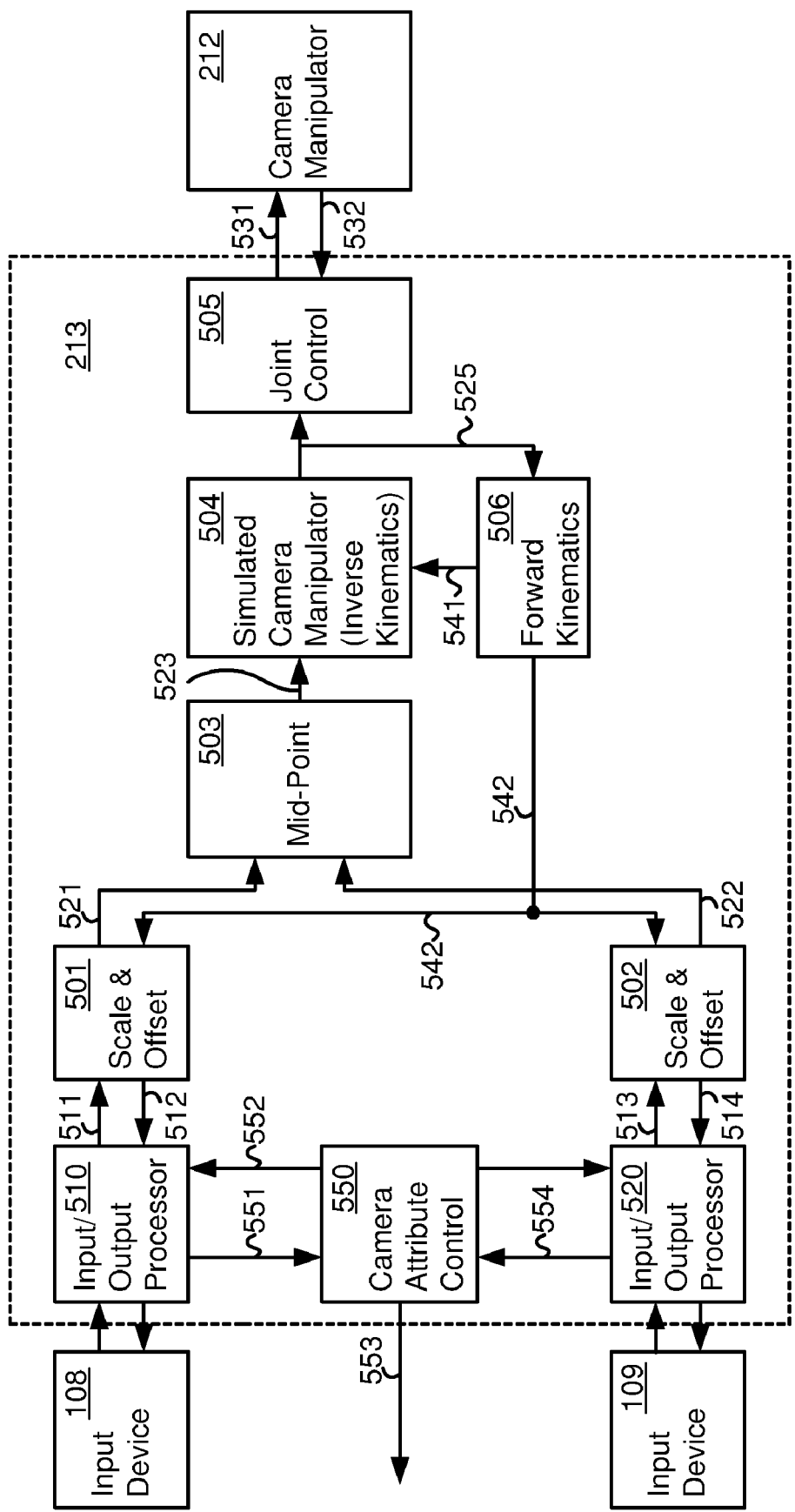
FIG. 5 illustrates a block diagram of a camera controller in a medical robotic system utilizing aspects of the present invention.

FIG. 5 illustrates, as an example, a block diagram of the camera controller 213 for controlling movement of the camera 140 through the camera manipulator 212 in response to operator manipulation of the master controls 108, 109 when they are selectively associated with the camera 140 to operate together in a cooperative fashion as a "virtual handlebar".

Each of the master controls 108, 109 includes a number of links connected by joints so as to facilitate multiple degrees-of-freedom movement. For example, as the Surgeon moves the master controls 108, 109 from one position to another, sensors associated with the joints of the master controls 108, 109 sense such movement at sampling intervals (appropriate for the processing speed of the processor 102) and provide digital information indicating such sampled movement in joint space to input/output processing blocks 510, 520.

Input/output processing blocks 510, 520 process the information received from the joint sensors of the master controls 108, 109 to transform the information into corresponding desired positions and velocities for the image being displayed on the monitor 104 in a Cartesian space relative to a reference frame associated with the Surgeon's eyes (the "eye reference frame") by computing, for example, joint velocities from the joint position information (or, alternatively, receiving velocity information from velocity sensors in the master controls 108, 109) and performing the transformation using a Jacobian matrix and eye related information using well-known transformation techniques.

Scale and offset processing blocks 501, 502 receive the processed information 511, 513 from the input processing blocks 510, 520, convert the desired positions and velocities to positions and velocities of the camera tip 141 in the remote center reference frame 400 (as shown and described in reference to FIG. 4), and apply scale and offset adjustments to the information so that the resulting movement of the camera tip 141 and consequently, the image being viewed on the monitor 104 appears natural and as expected by the operator of the master controls 108, 109.

The scale adjustment is useful where small movements of the camera tip 141 are desired relative to larger movement of the master controls 108, 109 in order to allow more precise movement of the camera tip 141 as it views the work site. To implement the shared control for moving the camera tip 141 by the master controls 108, 109, lateral offsets are applied to shift the control point to the left for the input device 108 which is being operated by the left hand of the operator and to the right for the input device 109 which is being operated by the right hand of the operator so that each of the master controls 108, 109 appears to control a corresponding (i.e., left or right) view of the stereoscopic image being displayed on the monitor 104. In addition, offset adjustments are applied for aligning the master controls 108, 109 with respect to the Surgeon's eyes as he or she manipulates the master controls 108, 109 to command movement of the camera tip 141 and consequently, its captured image that is being displayed at the time on the monitor 104.

The outputs 521, 522 of the scale and offset blocks 501, 502 are provided to a mid-point generation block 503 so that a single set of position and velocity commands for the camera tip 141 in the remote center reference frame 400 is provided for the camera manipulator 212. Therefore, as the operator moves the master controls 108, 109, he or she forces a motion relative to a mid-point (i.e., mid-point 320 in FIG. 3) of what feels like to the operator to be a "virtual handlebar". Note that under this type of control, the image on the monitor 104 appears to move in opposite directions in response to movement of the master controls 108, 109. For example, the image moves to the right when the master controls 108, 109 are moved to the left (and vice versa) and the image moves up when the master controls 108, 109 are moved down (and vice versa).

Figure 6:
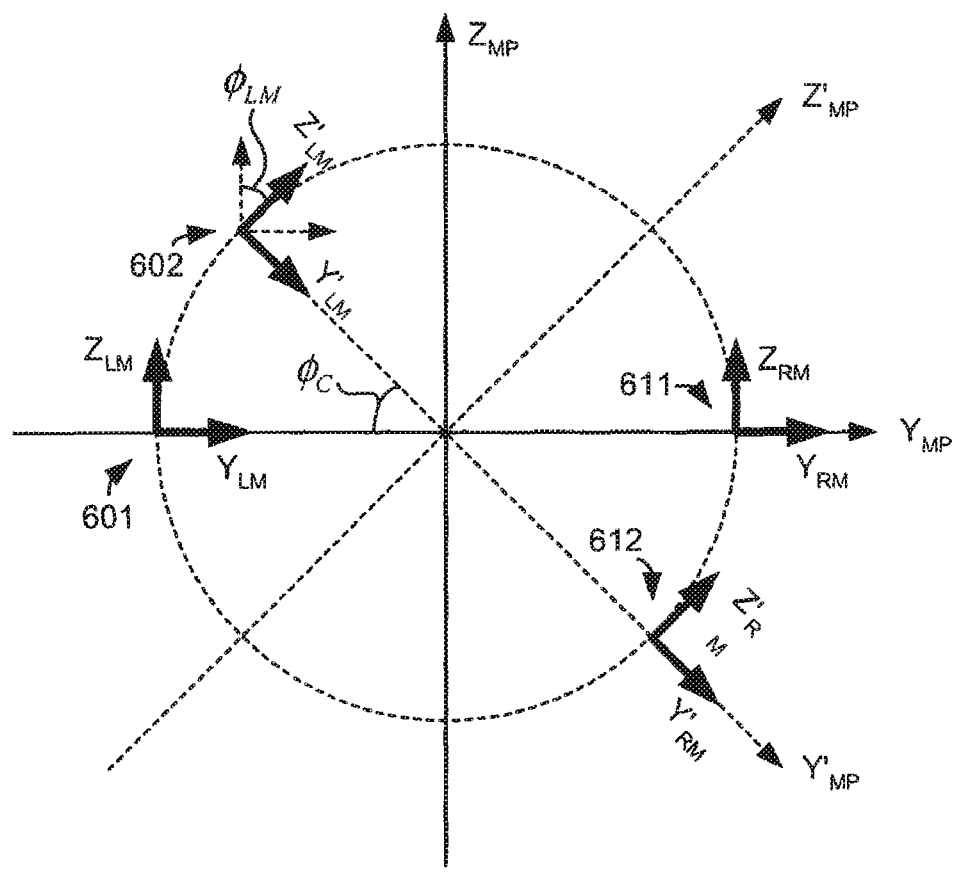
FIG. 6 illustrates a graphic diagram of a camera roll maneuver using a pair of master controls cooperatively operating as a virtual handlebar in a medical robotic system utilizing aspects of the present invention.

A simulated camera manipulator block 504 receives the output 523 of the mid-point generation block 503 and transforms the commanded position and velocity for the camera tip 141 from its Cartesian space to corresponding desired joint positions and velocities for the camera manipulator 212 using known inverse kinematics of the camera manipulator 212 and the geometry of the camera 140. In doing so, the simulated camera manipulator block 504 avoids singularities, limits the commanded joint positions and velocities to avoid physical limitations, and implements aspects of the "virtual handlebar" scheme through translational and rotational movements such as described in reference to FIG. 6.

The output 525 of the simulated camera manipulator block 504, which includes a commanded value for each joint of the camera manipulator 212, is provided to a joint controller block 505 and a forward kinematics block 506. The joint controller block 505 includes a joint control system for each controlled joint of the camera manipulator 212 (i.e., mechanical elements controlling the four degrees-of-freedom described in reference to FIG. 4).

For feedback control purposes, sensors associated with each of the controlled joints of the camera manipulator 212 provide sensor data 532 back to the joint controller block 505 indicating the current position and/or velocity of each joint of the camera manipulator 212. The sensors may sense this joint information either directly (e.g., from the joint on the camera manipulator 212) or indirectly (e.g., from the actuator in the camera manipulator 212 driving the joint). Each joint control system in the joint controller 505 then generates a torque or other appropriate command for its respective actuator (e.g., motor) in the camera manipulator 212 so as to drive the difference between the commanded and sensed joint values to zero in a conventional feedback control system manner.

The forward kinematics block 506 transforms the output 525 of the simulated camera manipulator block 504 from joint space back to the Cartesian space of the camera tip 141 in the remote center reference frame 400 using the forward kinematics of the camera manipulator 212 and the known geometry of the camera 140.

The scale and offset blocks 501, 502 perform inverse scale and offset functions on the output 542 of the forward kinematics block 506 (as well as performing a reversal of the mid-point generation) before passing their respective outputs 512, 514 to the input/output processing blocks 510, 520 where error values are calculated between their respective outputs 511, 513 and inputs 512, 514. If no limitation or other constraint had been imposed on the input 523 to the simulated camera manipulator block 504, then the calculated error values would be zero. On the other hand, if a limitation or constraint had been imposed, then the error value is not zero and it is converted to a torque command that drives actuators in the master controls 108, 109 to provide force feedback felt by the hands of their operator. Thus, the operator becomes aware that a limitation or constraint is being imposed by the force that he or she feels resisting his movement of the master controls 108, 109 in that direction. In addition to this force feedback, forces coming from other sensors or algorithms may be superimposed on the force feedback as described herein.

An output 541 of the forward kinematics block 506 may also be provided to the simulated camera manipulator block 504 for control purposes. For example, the simulated position output may be fed back and compared with the commanded position.

Also included in the camera controller 213 is a camera attribute control block 550 which adjusts a camera attribute, such as its focusing, using an otherwise unused degree-of-freedom of the master control 108, such as its master roll (i.e., operator rotation of the gripper 301 about the master's $X_{LM}$ axis). In addition to adjusting the camera attribute, the camera attribute control block 550 returns haptic feedback to the master control 108 through the input/output processing block 510 to assist the operator in effectively adjusting the camera attribute. Additional details on the construction and operation of the camera attribute control block 550 are described below in reference to FIGS. 7-10.

One problem to be addressed and overcome, however, before using the master roll for adjusting a camera attribute is that movement of the camera tip 241 may result in changing the master roll control setting (i.e., "master roll set-point") even without operator input on the master roll control. For example, in FIG. 6, the reference frames of the left and right master controls 108, 109 are respectively shown in corresponding first positions 601, 611 relative to the "virtual handlebar" reference frame 300 indicated by solid line axes $Z_{MP}$, $Y_{MP}$. To cause rotation of the camera 140 about its longitudinal axis by a roll angle $\phi_C$, the left and right master controls 108, 109 are moved by their operator as shown to second positions 602, 612 along with their "virtual handlebar" reference frame 300 indicated by dotted line axes $Z'_{MP}$, $Y'_{MP}$. As can be seen in this example, if the left and right master controls 108, 109 are constrained by the controller 213 through feedback to turn like a car steering wheel with the driver's thumbs in fixed positions relative to the steering wheel, the reference frames for the left and right master controls 108, 109 must also rotate by the same angle (as shown for the left master control 108 where its grip's roll rotation angle is equal to the camera's roll rotation angle, i.e., $\phi_{LM} = \phi_C$).

Thus, the set-point for the master roll angle changes by $\phi_{LM}$ in this example after the described roll maneuver. In general, the set-point is a state (e.g., position) that the torque control system in each of the input/output processing blocks 510, 520 drives its respective master control to in order to eliminate the Cartesian input error resulting from differences between the camera tip 241 position and orientation that are being commanded by the two master controls 108, 109 and the camera tip 241 position and orientation that corresponds to the output of the simulated camera manipulator block 504. Thus, once the camera tip 241 stops moving and the operator releases the master roll control, the master roll set-point is a neutral position that the camera manipulator 213 will drive itself to so that no torque is applied to the master controls 108, 109.

Figure 7A:
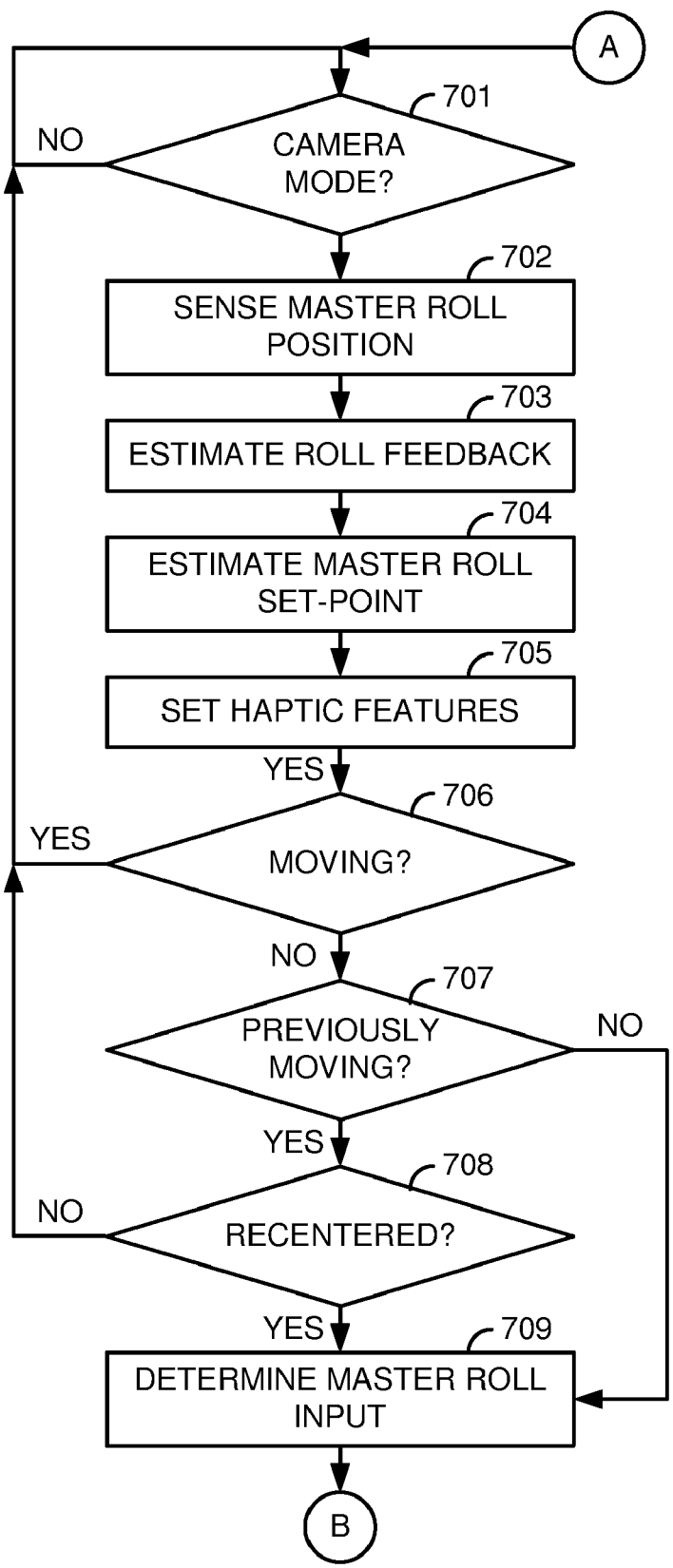
FIGS. 7a-b illustrate a method for adjusting an image capturing device attribute using an unused degree-of-freedom of a master control device, utilizing aspects of the present invention.
Figure 7B:
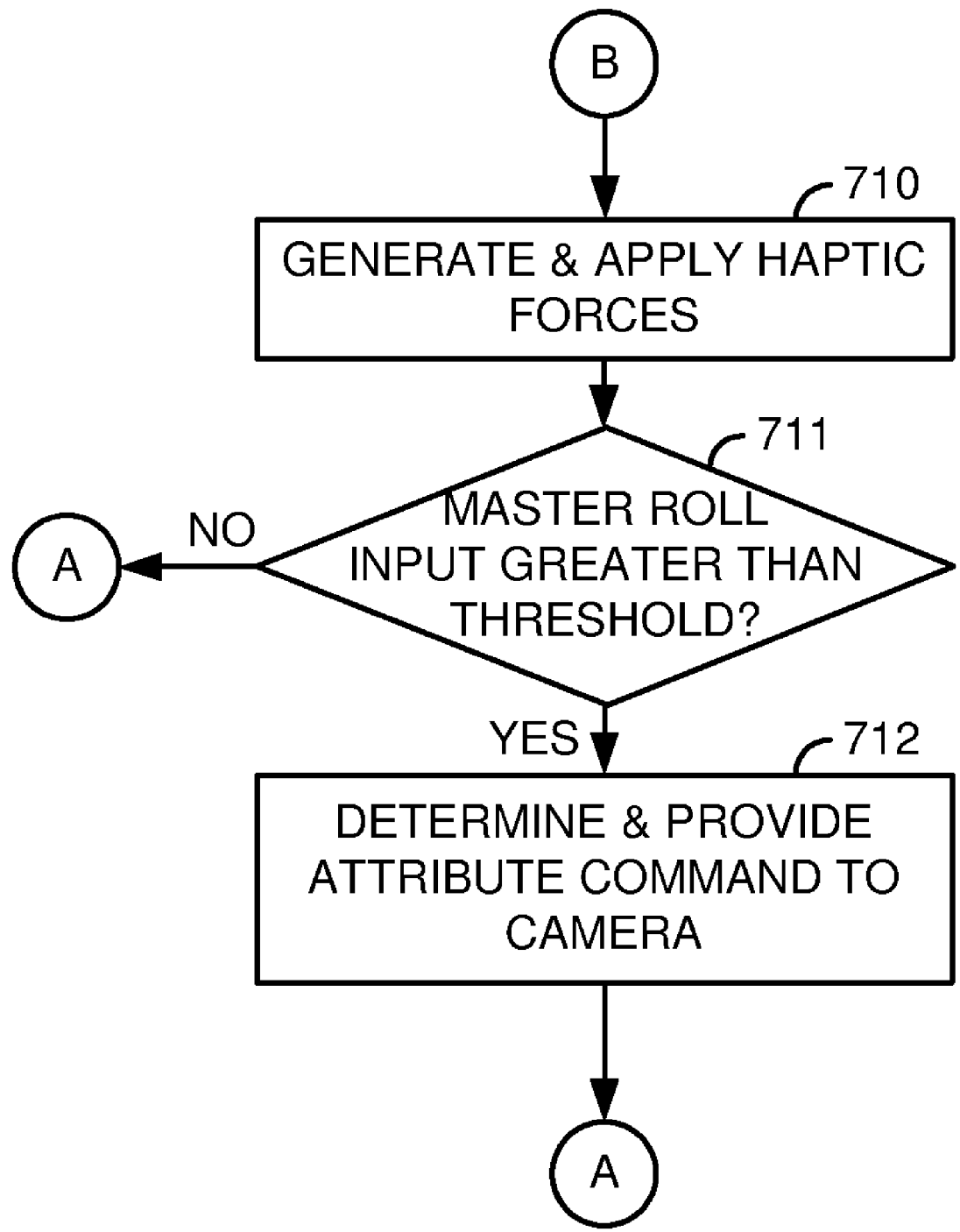

FIGS. 7a-b illustrate, as an example, a method (implemented, for example, in the camera attribute control block 550) for adjusting an image capturing device attribute using an unused degree-of-freedom of a master control device. Although the method is described as operating with the left master control 108, it is to be appreciated that the method may also be practiced using the right master control 109 or using a combination of the master controls 108, 109. Also, although the method is described as using the master roll (i.e., rotating the gripper 301 about its longitudinal $X_{LM}$ axis) for adjusting the camera attribute, it is to be appreciated that the method may also use any other appropriate unused degree-of-freedom of the master control 108. Further, although the method is described as adjusting a camera attribute, it may also be used for adjusting attributes or characteristics of other devices as well. Thus, any equations presented herein are to be understood to be applicable to any unused degree-of-freedom for image capturing device attribute control and/or adjustment, not just the master roll.

Starting with FIG. 7a, in 701, a determination is first made whether or not the medical robotic system 100 is operating in the camera positioning mode as described in reference to FIG. 2 with the switches 258, 259 in their respective "C2" and "C1" positions.

If the determination in 701 is NO, then the method periodically rechecks 701 (e.g., at the processing rate, or at a multiple of the processing rate, of the processor 102) until the system 100 is determined to be in its camera positioning mode. After the system 100 is determined in 701 to be in its camera positioning mode, in 702, the current master roll position $q_{SENSED}$ is determined from information generated by a sensor preferably in the master control 108 which detects positional rotation of the gripper 301 about its longitudinal $X_{LM}$ axis. The sensor information in this case may be passed through or generated within the input/output processing block 510 and transmitted over data path 551 to the camera attribute control block 550.

In 703, the roll feedback error is estimated. As previously explained, the master controls 108, 109 are controlled by torque feedback. Therefore, position feedbacks for the unused degrees-of-freedom are not directly available. Further, since each of the master controls 108, 109 is a kinematically redundant manipulator, there is no one-to-one mapping from its reference frame's six Cartesian coordinates to its seven joints. Therefore, to estimate the roll feedback error, the following equation (which has theoretical basis and has been found to have practical applicability in the present medical robotic system) is used which represents a change in roll angle that the torque will drive the master roll to in order to eliminate the Cartesian error:

$$\Delta q_{FB} = J^T e \quad (1)$$

where $\Delta q_{FB}$ is the roll feedback error, $J^T$ is the transpose of the Jacobian matrix for the master control 108, and e is the Cartesian error vector (received, for example, over data path 551 from the input/output processing block 510). Note that in calculating the roll feedback error $\Delta q_{FB}$ using equation (1), only the row of $J^T e$ which corresponds to the master roll is used.

In 704, the master roll set-point $q_{SP}$ is then estimated by adding the roll feedback error $\Delta q_{FB}$ to the current roll position $q_{SENSED}$ as follows:

$$q_{SP} = q_{SENSED} + \Delta q_{FB} \quad (2)$$

In 705, haptic features are set for a haptic force engine (included, for example, in the input/output processing block 510 with a corresponding engine in the input/output processing block 520) that generates master torque commands relative to the set-point $q_{SP}$, as described below in reference to FIG. 9, for the joint actuators of the master control device 108.

In 706, a determination is made as to whether or not the camera 140 is being positioned or oriented at the time. This determination is performed, because it is generally not desirable to adjust camera attributes until after such positioning and/or orienting has been substantially completed.

One way the determination may be performed in 706 is to determine whether the camera tip 141 is moving in any one of its degrees-of-freedom greater than a threshold velocity. For example, the determination may be based upon whether an insertion/retraction of the camera tip 141 is moving greater than a threshold velocity or whether a rotation of the camera tip 141 about its remote center 410 is rotating faster than a threshold rate. Alternatively, the determination may be made by calculating velocities of the individual master controls and using their combined velocities to determine whether significant movement is occurring. As another alternative, the velocity of the focal point may be used.

As an example of performing 706, a velocity metric v may be defined as follows that covers the movement of both master controls 108, 109 and compared with a predetermined threshold velocity:

$$v = v_{RM} + v_{LM} \quad (3)$$

where the velocities, $v_{LM}$, $v_{RM}$ are calculated each process cycle from changes in X, Y, Z master reference frame coordinate positions (received, for example, over data paths 551, 554 from input/output processing blocks 510, 520) since the previous process cycle for the left and right master controls 108, 109 as follows:

$$v_{LM} = \frac{\sqrt{(\Delta X_{LM})^2 + (\Delta Y_{LM})^2 + (\Delta Z_{LM})^2}}{\Delta t} \quad (4)$$

$$v_{RM} = \frac{\sqrt{(\Delta X_{RM})^2 + (\Delta Y_{RM})^2 + (\Delta Z_{RM})^2}}{\Delta t} \quad (5)$$

where $\Delta t$ is the time between process cycles.

Note that even though the combined movement of the master controls 108, 109 may have stopped moving faster than the threshold velocity, the camera tip 241 may continue to move too fast due to error control in the input/output processing block 610. Thus, the roll feedback error is also preferably checked against a corresponding velocity threshold.

To prevent false determinations due to hand tremor or other inadvertent small, but fast movements of the master control 108, a hand-tremor filter may also be included and/or a threshold for position change may be imposed (e.g., a deadband).

If the determination in 706 is that the camera tip 141 is moving faster than a threshold velocity (i.e., the determination in 706 is YES), then the method loops back to 701. On the other hand, if the determination in 706 is that the camera tip 141 is not moving faster than the threshold velocity (i.e., the determination in 706 is NO), then in 707, the method next determines whether the camera tip 141 had previously been moving (i.e., moving faster than the threshold velocity), stopped (i.e., moving less than the threshold velocity) and restarted moving again (i.e., moving faster than the threshold velocity again after being stopped) before detecting the current stoppage (i.e., moving less than the threshold velocity again). One way such a determination may be made is by setting and resetting one or more flags in a conventional manner indicating the prior state(s) of such movement of the camera tip 241. To avoid inadvertent switching of the flag due to noise and/or other random effects, conventional filtering techniques may be employed.

If the determination in 707 is NO (the camera was not previously moving), then the method proceeds to 709. On the other hand, if the determination in 707 is YES (i.e., the camera was previously moving, stopped and restarted), then in 708, a determination is made whether or not the master roll has been recentered to the set-point. One way for recentering to occur is for the operator to simply release the master control so that the normal control feedback 901 causes the master roll to return to the set-point. If the master roll has not recentered (i.e., the determination in 708 is NO), then the method suppresses adjustment of the camera attribute and jumps back to 701 to loop through 701-708 until the master roll is recentered. Once the master roll is determined to have been recentered (i.e., the determination in 708 is YES), then the method proceeds to 709.

In 709, the master roll input $\Delta q_{IN}$ is then determined according to the following equation:

$$\Delta q_{IN} = q_{SENSED} - q_{SP} \quad (6)$$

where the values for the current master roll position $q_{SENSED}$ and the set-point $q_{SP}$ are the ones determined respectively in 702 and 704.

In 710 (following connection B to FIG. 7b), the master roll input $\Delta q_{IN}$ is provided to the haptic force engine in the input/output processing block 510 so that haptic forces are generated according to the haptic features set in 705 and applied to the gripper 301 of the master control device 108 through generated torques on the master's joint actuators. A description of the applied haptic forces is described in reference to FIG. 9.

In order to prevent the operator from inadvertently adjusting the camera attribute, a deadband is defined around the set-point $q_{SP}$. Since it is desirable to notify the operator when the master roll input $\Delta q_{IN}$ is about to exit the deadband and start adjustment of the camera attribute, in 711, a determination is made whether the absolute value of the master roll input $\Delta q_{IN}$ is greater than the absolute value of the threshold value $q_{TH}$ on either side of the deadband. If the determination in 711 is NO, then the method loops back to 701 (following connection A back to FIG. 7a) and performs 701-711 (or 701-712) for a next process cycle.

On the other hand, if the determination in 711 is YES (i.e., the absolute value of the master roll input $\Delta q_{IN}$ is greater than the absolute value of the threshold $q_{TH}$ on either side of the deadband), then the method proceeds to 712. In 712, the method determines the attribute adjustment command and provides it to the camera 140 (through, for example, data path 553). The attribute command may be generated, for example, using the following equation:

$$\text{Command} = f(\Delta q_{IN} - q_{TH}) \text{ for } |\Delta q_{IN}| \rangle q_{TH} \quad (7)$$

where the function $f(x)$ is a monotonic increasing function, such as a straight line with positive slope passing through zero (i.e., where the master roll input $\Delta q_{IN}$ equals the threshold $q_{TH}$). After 712, the method then loops back to 701 (following connection A back to FIG. 7a) and performs 701-712 for a next processing cycle.

Figure 8A:
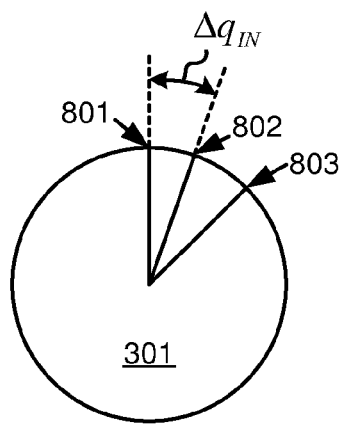
FIGS. 8a-8c illustrate master roll input, set-point, and threshold positions as used in a medical robotic system utilizing aspects of the present invention.
Figure 8B:
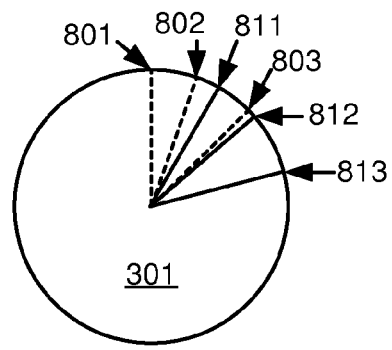
Figure 8C:
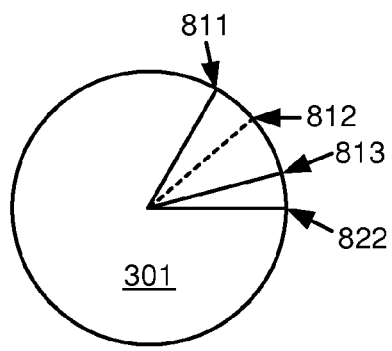

FIGS. 8a-8c illustrate, as examples, a front view of the gripper 301 (i.e., along the axial direction $X_{LM}$) with various master roll input positions and corresponding set-points and thresholds. In FIG. 8a, a set-point $q_{SP}$ 801 is shown with a master roll input position $\Delta q_{IN}$ 802 that is between the set-point $q_{SP}$ 801 and a threshold value $q_{TH}$ 803. In FIG. 8b, the set-point $q_{SP}$ formerly at 801 has now moved to 811 (due to repositioning of the camera tip 241 such as described in reference to FIG. 6), and as a result, the position of the master roll input $\Delta q_{IN}$ formerly at 802 has moved to 812 and position of the threshold value $q_{TH}$ formerly at 803 has effectively moved to 813. In FIG. 8c, the master roll input $\Delta q_{IN}$ formerly at 812 has now moved to 822, which is beyond the threshold value $q_{TH}$ at 813 so that adjustment of the camera attribute has begun.

Figure 9:
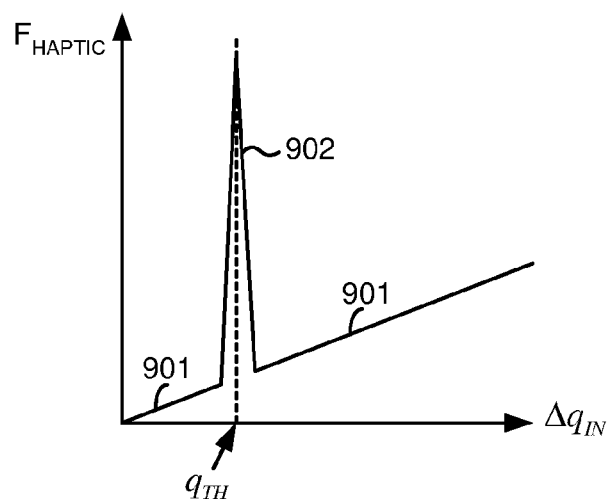
FIG. 9 illustrates a diagram for a haptic force vs. master roll input relationship as used in a medical robotic system utilizing aspects of the present invention.

FIG. 9 illustrates, as an example, a diagram for a haptic force ($F_{HAPTIC}$) vs. master roll input ($\Delta q_{IN}$) relationship as used in the input/output processing block 510 for providing torque feedback to the master control 108. A first component 901 of the torque feedback arises from normal control feedback so that as the master roll is manipulated past its neutral point (i.e., set-point), a restoring force results that returns the master roll to its neutral point after the master roll (i.e., rotation of the gripper 301 about its longitudinal $X_{LM}$ axis) is released. A second component 902 is a haptic peak force command generated in the camera attribute control block 550 when the master roll is manipulated by the operator so that the roll input $\Delta q_{IN}$ nears the outer boundaries (i.e., the threshold values $+q_{TH}$, $-q_{IN}$) of a deadband region. As shown in the figure, the second component 902 is superimposed on the first component 901. Note that this a peak haptic force 902 is provided back to the gripper 301 of the master control 108 as the master roll nears and passes through the threshold so that it feels to the operator like a radio knob turning the radio ON before changing the volume.

Figure 10:
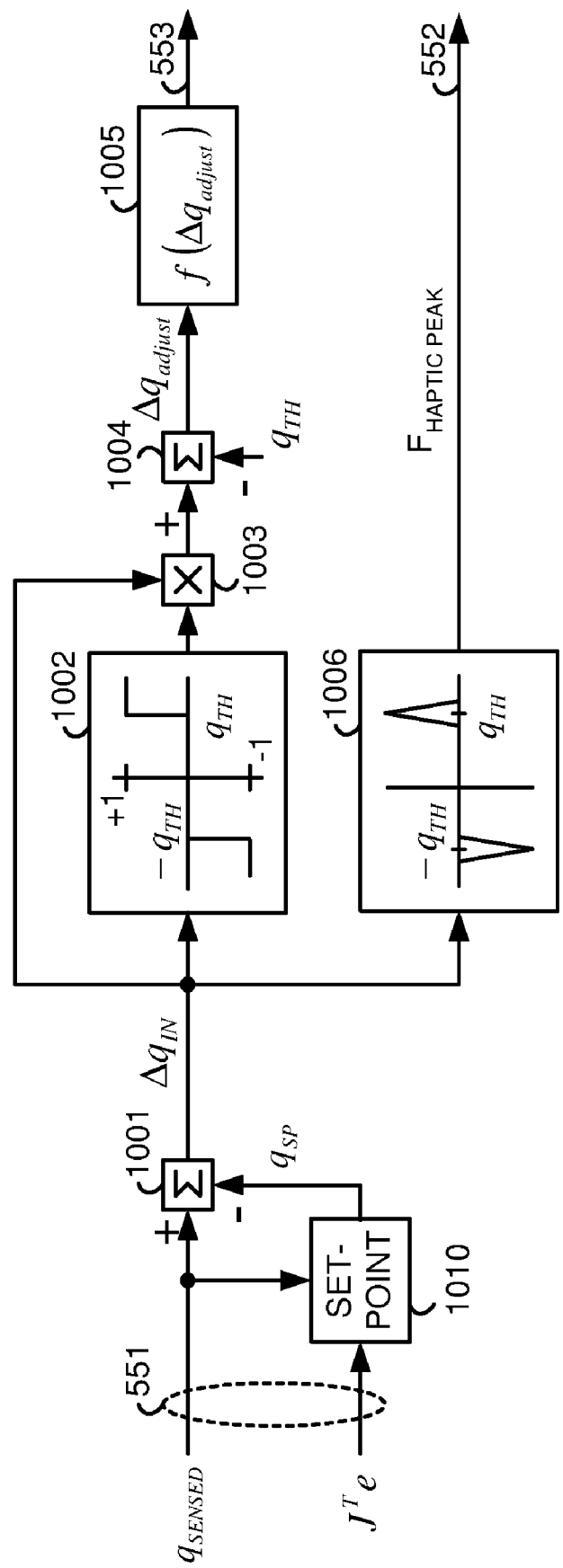
FIG. 10 illustrates a block diagram of a camera attribute control unit used in a medical robotic system utilizing aspects of the present invention.

FIG. 10 illustrates, as an example, a block diagram of the camera attribute control block 550. A set-point generation block 1010 generates and stores the master roll set-point $q_{SP}$ according to the method described in reference to 702-704 of FIG. 7a. The master roll input $\Delta q_{IN}$ is generated at node 1001 as the difference between the sensed master roll position $q_{SENSED}$ and the set-point $q_{SP}$ in accordance with the method described in reference to 709 of FIG. 7a. The master roll input $\Delta q_{IN}$ is then applied to a first path that generates the camera attribute command output 553 being provided to the camera 140 and a second path that generates the peak haptic feedback command 552.

To generate the attribute command output 553 in the first path, the master roll input $\Delta q_{IN}$ is provided to a deadband function 1002, which has an output equal to +1 when the master roll input $\Delta q_{IN}$ is greater than the threshold value $+q_{TH}$ and an output equal to $-1$ when the master roll input $\Delta q_{IN}$ is less than the threshold value $-q_{TH}$. In the deadband area between threshold values $+q_{TH}$ and $-q_{TH}$, the output is zero. A multiplier 1003 generates a product by multiplying the output of the deadband function 1002 with the master roll input $\Delta q_{IN}$.

A summing node 1004 generates an adjusted master roll input $\Delta q_{adjust}$ by subtracting the threshold value $q_{TH}$ from the product generated by the multiplier 1003. The adjusted master roll input $\Delta q_{adjust}$ is then applied to a function block 1005 which generates as its output 553 the command to the adjust the camera attribute according to equation (7) above.

To generate the haptic feedback command 552 in the second path, a haptic peak force generating block 1006 generates a peak force as described in reference to the peak force 902 in reference to FIG. 9. The haptic force feedback command 552 is then provided back to the haptic force engine in the input processing block 510 so that it may generate and provide an appropriate torque feedback on the master roll actuator associated with the gripper 301 of the master control 108.

Although the various aspects of the present invention have been described with respect to a preferred embodiment, it will be understood that the invention is entitled to full protection within the full scope of the appended claims.

We claim:

1. A medical robotic system comprising:
   an image capturing device manipulatable relative to a first reference frame in a first plurality of degrees-of-freedom;
   a first master control device manipulatable relative to a second reference frame in a second plurality of degrees-of-freedom; and
   a controller adapted to:
      command manipulation of the image capturing device in each of the first plurality of degrees-of-freedom according to input received from the first master control device using less than all of the second plurality of degrees-of-freedom;
      initially determine and periodically update a set-point for an unused one of the second plurality of degrees-of-freedom of the first master control device, wherein the periodic updating is performed by sensing a position of the unused one of the second plurality of degrees-of-freedom of the first master control device, estimating a feedback error resulting from controlling the manipulation of the image capturing device wherein the feedback error effects a change in the set-point of the unused one of the second plurality of degrees-of-freedom of the first master control device, and determining the updated set-point using the sensed position and the estimated feedback error, and wherein the set-point is a state of the unused one of the second plurality of degrees-of-freedom of the first master control device and the set-point changes as one or more of the used ones of the second plurality of degrees-of-freedom of the first master control device is used to command manipulation of the image capturing device; and
      adjust an attribute of the image capturing device in response to manipulation of the first master control device in the unused one of the second plurality of degrees-of-freedom of the first master control device relative to the periodically updated set-point.

2. The medical robotic system according to claim 1, wherein the controller is adapted to adjust the attribute of the image capturing device only if the image capturing device is not being manipulated so as to be moving faster than a threshold velocity.

3. The medical robotic system according to claim 1, wherein the controller is adapted to adjust the attribute of the image capturing device only if the first master control device is not being manipulated so as to be moving faster than a threshold velocity.

4. The medical robotic system according to claim 1, further comprising:
  a second master control device manipulatable relative to a third reference frame in a third plurality of degrees-of-freedom;
  wherein the controller is adapted to command manipulation of the image capturing device in each of the first plurality of degrees-of-freedom according to inputs received from the first and second master control devices.

5. The medical robotic system according to claim 4, wherein a pivot point of the first master control device serves as an origin of the first reference frame, a pivot point of the second master control device serves as an origin of the second reference frame, and the controller is adapted to command manipulation of the image capturing device in each of the first plurality of degrees-of-freedom according to manipulation of the first and second master control devices relative to a fourth reference frame having its origin mid-way between the pivot points of the first and second master control devices.

6. The medical robotic system according to claim 1, wherein the controller is adapted to estimate the feedback error using the transpose of a Jacobian of the first master control device.

7. The medical robotic system according to claim 1, wherein the controller is adapted to adjust the attribute of the image capturing device using a difference between a sensed current state of the unused one of the second plurality of degrees-of-freedom of the first master control device and the periodically updated set-point.

8. The medical robotic system according to claim 7, wherein the controller is adapted to adjust the attribute of the image capturing device only after the absolute value of the difference between the sensed current state and the periodically updated set-point exceeds a threshold value.

9. The medical robotic system according to claim 8, wherein the controller is adapted to command a peak force to be felt on the first master control device so as to be associated with the unused one of the second plurality of degrees-of-freedom as the absolute value of the difference reaches the threshold value.

10. The medical robotic system according to claim 8, wherein the controller is adapted to adjust the attribute of the image capturing device according to an amount by which the absolute value of the difference exceeds the threshold value.

11. A method for adjusting an attribute of an image capturing device that is robotically manipulatable relative to a first reference frame in a first plurality of degrees-of-freedom, comprising:
  controlling robotic manipulation of the image capturing device in each of the first plurality of degrees-of-freedom according to at least an input received from a first master control device manipulatable in a second reference frame in a second plurality of degrees-of-freedom, wherein the robotic manipulation of the image capturing device uses less than all of the second plurality of degrees-of-freedom;
  initially determining and periodically updating a set-point for an unused one of the second plurality of degrees-of-freedom of the first master control device, wherein the periodic updating is performed by sensing a position of the unused one of the second plurality of degrees-of-freedom of the first master control device, estimating a feedback error resulting from the controlling of the robotic manipulation of the image capturing device wherein the feedback error effects a change in the set-point of the unused one of the second plurality of degrees-of-freedom of the first master control device, and determining the updated set-point using the sensed position and estimated feedback error, and wherein the set-point is a state of the unused one of the second plurality of degrees-of-freedom of the first master control device and the set-point changes as one or more of the used ones of the second plurality of degrees-of-freedom of the first master control device is used; and
  adjusting the attribute of the image capturing device in response to manipulation of the first master control device in the unused one of the second plurality of degrees-of-freedom of the first master control device relative to the periodically updated set-point.

12. The method according to claim 11, wherein the adjusting of the attribute of the image capturing device is performed only if the image capturing device is not being manipulated so as to be moving faster than a threshold velocity.

13. The method according to claim 11, wherein the adjusting of the attribute of the image capturing device is performed only if the first master control device is not being manipulated so as to be moving faster than a threshold velocity.

14. The method according to claim 11, wherein the controlling of the robotic manipulation of the image capturing device in each of the first plurality of degrees-of-freedom is according to the input received from the first master control device and an input received from a second master control device manipulatable relative to a third reference frame in a third plurality of degrees-of-freedom.

15. The method according to claim 14, wherein an origin of the first reference frame is a pivot point of the first master control device, an origin of the second reference frame is a pivot point of the second master control device, and the inputs received from the first and second master control devices are relative to a fourth reference frame having its origin mid-way between the pivot points of the first and second master control devices.

16. The method according to claim 11, wherein the estimating of the feedback error uses the transpose of a Jacobian of the first master control device.

17. The method according to claim 11, wherein the adjusting of the attribute of the image capturing device uses a difference between a sensed current state of the unused one of the second plurality of degrees-of-freedom of the first master control device and the periodically updated set-point.

18. The method according to claim 17, wherein the adjusting of the attribute of the image capturing device is performed only after the absolute value of the difference between the sensed current state and the periodically updated set-point exceeds a threshold value.

19. The method according to claim 18, further comprising:
  commanding a peak force to be felt on the first master control device in the unused one of the second plurality of degrees-of-freedom of the first master control device as the absolute value of the difference reaches the threshold value.

20. The method according to claim 18, wherein the adjusting of the attribute of the image capturing device is performed according to an amount by which the absolute value of the difference exceeds the threshold value.

21. A medical robotic system comprising:
  an image capturing device;
  a slave manipulator adapted to manipulate the image capturing device in four degrees-of-freedom;
  first and second master control devices each manipulatable in six degrees-of-freedom about its pivot point and cooperatively manipulatable in six degrees-of-freedom about a mid-point between the pivot points of the first and second master control devices; and a controller adapted to:

command manipulation of the image capturing device according to the cooperative manipulation of the first and second master control devices;

initially determine and periodically update a set-point of an unused one of the six degrees-of-freedom of the first master control device, wherein the periodic updating is performed by sensing a position of the unused one of the six of degrees-of-freedom of the first master control device, estimating a feedback error resulting from controlling the manipulation of the image capturing device wherein the feedback error effects a change in the set-point of the unused one of the six degrees-of-freedom of the first master control device, and determining the updated set-point using the sensed position and estimated feedback error, and wherein the set-point is a state of the unused one of the six degrees-of-freedom of the first master control device and the set-point changes as one or more of the used ones of the six degrees-of-freedom of the first master control device is use; and adjust an attribute of the image capturing device in response to manipulation of the first master control device in the unused one of the six degrees-of-freedom of the first master control device relative to the periodically updated set-point.

22. The medical robotic system according to claim 21, wherein the first master control device has a gripper and the unused one of the six degrees-of-freedom of the first master control device is a roll rotation about a longitudinal axis of the gripper.

23. The medical robotic system according to claim 21, wherein the image capturing device is a camera and the attribute of the image capturing device is its focus.

24. The medical robotic system according to claim 21, wherein the controller is adapted to adjust the attribute of the image capturing device only if a velocity metric based upon the movements of the first and second master input devices is less than a threshold velocity.

25. The medical robotic system according to claim 24, wherein the velocity metric is the absolute value of a combination of the velocities of the first and second master input devices.

26. The medical robotic system according to claim 21, wherein the controller is adapted to estimate the feedback error using the transpose of a Jacobian of the first master control device.

27. The medical robotic system according to claim 21, wherein the controller is adapted to adjust the attribute of the image capturing device using a difference between a sensed current state of the unused one of the six degrees-of-freedom of the first master control device and the periodically updated set-point.

28. The medical robotic system according to claim 27, wherein the controller is adapted to adjust the attribute of the image capturing device only after the absolute value of the difference between the sensed current state and the periodically updated set-point exceeds a threshold value.

29. The medical robotic system according to claim 28, wherein the controller is adapted to command a peak force to be felt on the first master control device so as to be associated with the unused one of the six degrees-of-freedom of the first master control device as the absolute value of the difference reaches the threshold value.

30. The medical robotic system according to claim 28, wherein the controller is adapted to adjust the attribute of the image capturing device according to an amount by which the absolute value of the difference exceeds the threshold value.

* * * * *